United States Patent
Miller et al.

(10) Patent No.: US 11,079,452 B2
(45) Date of Patent: Aug. 3, 2021

(54) SYSTEMS AND METHODS FOR MAGNETIC RESONANCE THERMOMETRY USING BALANCED STEADY STATE FREE PRECESSION

(71) Applicant: University of Virginia Patent Foundation, Charlottesville, VA (US)

(72) Inventors: Grady Wilson Miller, Charlottesville, VA (US); Yuan Zheng, Fremont, CA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1199 days.

(21) Appl. No.: 15/506,169

(22) PCT Filed: Oct. 9, 2015

(86) PCT No.: PCT/US2015/055004
§ 371 (c)(1),
(2) Date: Feb. 23, 2017

(87) PCT Pub. No.: WO2016/057962
PCT Pub. Date: Apr. 14, 2016

(65) Prior Publication Data
US 2017/0281042 A1    Oct. 5, 2017

Related U.S. Application Data

(60) Provisional application No. 62/062,872, filed on Oct. 11, 2014.

(51) Int. Cl.
*A61B 5/01*    (2006.01)
*G01R 33/48*    (2006.01)
(Continued)

(52) U.S. Cl.
CPC ........ *G01R 33/4804* (2013.01); *A61B 5/0036* (2018.08); *A61B 5/015* (2013.01);
(Continued)

(58) Field of Classification Search
CPC ..................... G01R 33/4804; A61B 5/01–015
See application file for complete search history.

(56) References Cited

U.S. PATENT DOCUMENTS 7,078,903 B2   7/2006   Paliwal et al.
8,274,285 B2   9/2012   Bieri et al.
(Continued)

OTHER PUBLICATIONS

Chang-sheng et al. "Ultrafast 1D MR thermometry using phase or frequency mapping." MAGMA. Feb. 2012;25(1): 5-14. (Year : 2012).*

(Continued)

*Primary Examiner* — Luther Behringer
(74) *Attorney, Agent, or Firm* — Meunier Carlin & Curfman LLC

(57) ABSTRACT

Some aspects of the present disclosure relate to systems and methods for magnetic resonance thermometry. In one embodiment, a preliminary balanced steady state free precession (bSSFP) magnetic resonance imaging pulse sequence is applied to an area of interest of a subject. Based on bSSFP image phases, a relationship between frequency and image phase associated with the area of interest can be determined and a bSSFP magnetic resonance imaging pulse sequence applied for temperature change measurement during and/or after focused energy is applied to the subject. Based on image phase change associated with temperature change and using the determined relationship between frequency and image phase, a change in the resonance frequency associated with the target area due to the application of the focused energy can be determined, and the tempera- (Continued)

ture change can be determined based on the determined change in the resonance frequency.

15 Claims, 12 Drawing Sheets

(51) Int. Cl.
A61B 5/055 (2006.01)
G01R 33/561 (2006.01)
A61B 5/00 (2006.01)
(52) U.S. Cl.
CPC .......... A61B 5/055 (2013.01); G01R 33/5614 (2013.01); A61B 5/4836 (2013.01)

(56) References Cited

U.S. PATENT DOCUMENTS

| 2005/0052183 | A1* | 3/2005 | Paliwal | G01R 33/4804 324/315 |
| 2008/0194941 | A1* | 8/2008 | Steinmeyer | G01R 33/28 600/411 |
| 2010/0312094 | A1 | 12/2010 | Guttman et al. | |
| 2011/0234224 | A1* | 9/2011 | Bieri | G01R 33/5614 324/309 |

OTHER PUBLICATIONS

BierI, O. et al., "Fundamentals of Balanced Steady State Free Precession MRI," Journal of Magnetic Resonance Imaging, Wiley Periodicals, Inc., 2013, 38:2-11.
Chen, J. et al., "Investigation of Proton Density for Measuring Tissue Temperature," Journal of Magnetic Imaging, Resonance 2006, 23:430-434.
De Poorter, J. et al., "Noninvasive MRI Thermometry with the Proton Resonance Frequency (PRF) Method: In Vivo Results in Human Muscle," Magnetic Resonance Medicine, 1995, 33:74-81.
Gianfelice, D. et al., "Feasibililty of Magnetic Resonance Imaging-guided Focused Ultrasound Surgery as an Adjunct to Tamoxifen Therapy in High-Risk Surgical Patients with Breast Carcinoma," J. Vasc. Interv. Radiol., 2003, 14:1275-1282.
Graham, S. et al.,"Time and Temperature Dependence of MR Parameters during Thermal Coagulation of Ex Vivo Rabbit Muscle," Magnetic Resonance Medicine, 1998, 39:198-203.
Haacke, E. et al., "Magnetic Resonance Imaging Physical Principles and Sequence Design," Chapter 18.2, Short-TR, Coherent, Gradient Echo Imaging, Wiley-Liss, 1999, 31 pages.
Kennedy, James, E., "High-Intensity Focused Ultrasound in the Treatment of Solid Tumours," Nature, Apr. 2005, 5:321-327.
LeBihan, D. et al., "Temperature Mapping with MR Imaging of Molecular Diffusion: Application to Hyperthermia, Radiology," 1989, 171:853-857.
Lewin, J. et al., "Interactive MRI-Guided Radiofrequency Interstitial Thermal Ablation of Abdominal Tumors: Clinical Trial for Evaluation of Safety and Feasibility," Journal of Magnetic Resonance Imaging, 1998, 8:40-47.
Matsumoto, R. et al., "Tissue Temperature Monitoring for Thermal Interventional Therapy: Comparison of T1-Weighted MR Sequences," Journal of Magnetic Resonance Imaging, 1994, 4:65-70.
McDannold, N. et al, "Magnetic Resonance Acoustic Radiation Force Imaging," Med. Phys., 2008, 35:3748-3758.
Miller, K. et al., "Functional Brain Imaging Using a Blood Oxygenation Sensitive Steady State," Magnetic Resonance in Medicine, 2003, 50:675-683.
Nateras, O., SNR using balanced steady-state free precession (b-SSFP), Advanced Diagnostic Imaging (RADI 6016), May 14, 2010, [Retrieved Nov. 22, 2015], Retrieved From the Internet: <URL: http://ric.uthscsa.edu/personalpages/lancaster/D12_Projects_2010/bSSFP_SNR.pdf> Entire Document.
Paliwal, V. et al., "SSFP-Based MR Thermometry," Magnetic Resonance in Medicine, 2004, 52:704-708.
Rieke, V. et al., "Referenceless PRF Shift Thermometry," Magnetic Resonance in Medicine, 2004, 51:1223-1231.
Rieke, V. et al., "PRF shift thermometry using multiple-acquisition phase-cycled balanced SSFP," ISMRM Conference Abstract 2007, 1 page.
Scheffler, K., "Fast Frequency Mapping With Balanced SSFP: Theory and Application to Proton-Resonance Frequency Shift Thermometry," Magnetic Resonance in Medicine, 2004, 51:1205-1211.
Sequeiros, R. et al., "MR imaging-guided laser ablation of osteoid osteomas with use of optical instrument at guidance 0.23 T," Eur Radiol., 2003, 13:2309-2314.
Stewart, E. et al., "Focused ultrasound treatment of uterine fibroid tumors: Safety and feasibility of noninvasive thermoablative technique," Am J. Obstet. Gynecol, 2003, 189:48-54.
Tempany, C. et al., "Focused Ultrasound Surgery in Oncology: Overview and Principles," Radiology, 2011, 259:39-56.

* cited by examiner

SYSTEMS AND METHODS FOR MAGNETIC RESONANCE THERMOMETRY USING BALANCED STEADY STATE FREE PRECESSION

CROSS-REFERENCE TO RELATED APPLICATIONS

This application is a U.S. National Stage Application of, and claims the benefit pursuant to 35 U.S.C. § 371 of, International Patent Application No. PCT/US2015/055004, filed Oct. 9, 2015, which claims priority to U.S. Provisional Patent Application No. 62/062,872, filed Oct. 11, 2014, the entire contents and substance of which are incorporated herein by reference in their entirety as if fully set forth below.

Some references, which include various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

BACKGROUND

Magnetic resonance imaging (MRI) has been used to monitor temperature changes in the body during medical interventions such as radiofrequency (RF) ablation, laser ablation and focused ultrasound (FUS) therapy. The goal of such treatments is to deliver just enough thermal heating to destroy the target tissue without hurting surrounding tissue. Focused ultrasound is also used for non-ablative interventions, in which tissue heating is possible but is not the desired effect. It is therefore important to monitor the temperature change versus time over the region of interest (also referred to herein as an "area of interest"), to provide real-time feedback for ensuring both the safety and efficacy of any such medical interventions.

Magnetic resonance (MR) thermometry techniques make use of the fact that some MR parameters, such as proton density, T1 relaxation, T2 relaxation, diffusion coefficient, and the proton resonant frequency (PRF), depend on temperature. Image contrast based on these parameters can be generated using different pulse sequence strategies, which can in turn be used to determine the temperature change.

PRF-based thermometry of water-based tissues is the most widely used MR thermometry technique, primarily because the PRF shift depends linearly on temperature over a large temperature range (−15° C.-100° C.) and is fairly independent of the tissue type and thermal history. Spoiled gradient-recalled-echo (GRE) pulse sequences are typically used to perform PRF-based MR thermometry during thermal treatments ([1],[2]) because they provide straightforward and robust sensitivity to the PRF shift. Balanced steady-state free precession (bSSFP) pulse sequences have also been used to generate sensitivity to temperature-induced PRF shifts. Although some of these prior methods for MR thermometry have been applied in various contexts, including focused ultrasound, they are not ideal for detecting and quantifying small and/or fast temperature changes due to limited sensitivity and/or speed.

Spoiled GRE pulse sequences are commonly used for PRF shift based thermometry during thermal treatments ([1],[2]). The temperature measurement is usually accomplished by acquiring a time series of identical MR images. Baseline images are acquired before beginning the thermal treatment, and new images are acquired during the thermal treatment. In the resulting images, the temperature change ΔT from one image to another is related to the image phase change Δφ by:

$$\Delta T = \Delta\varphi/(\alpha\gamma B_0 TE) \qquad [\text{Eq. 1}]$$

where $B_0$ is the scanner field strength, γ is the $^1$H gyromagnetic ratio, TE is the echo time for the image acquisition, and a is the temperature coefficient. The sensitivity of the temperature-change measurement can be increased by increasing TE. However, in practice, TE is limited by T2* relaxation. Another practical concern is spatial distortion of the derived temperature map as any spatial distortion of the acquired images due to nonuniform magnetic fields will be amplified by using lower readout bandwidths often associated with a longer TE. Another practical concern is temporal resolution because the required repetition time TR, and therefore the total imaging time, increases with TE. That is, increasing sensitivity by increasing TE reduces the achievable temporal resolution of the temperature measurements. Accordingly, there are practical limits to the sensitivity and speed achievable with MR thermometry using a spoiled GRE pulse sequence.

Another existing bSSFP thermometry technique ([3]) incorporates multiple image acquisitions into the bSSFP pulse sequence by acquiring multiple echoes within each TR period. The image phases at these echoes are fitted to a line, and the slope of this fit indicates the PRF. This is the same principle used for spoiled-GRE techniques and yields the same temperature sensitivity, except the images happen to be collected using a bSSFP pulse sequence. The achievable temporal resolution of the technique of [4] is not ideal as multiple image acquisitions must be woven into each PRF shift measurement.

In another existing method for bSSFP thermometry ([4]), multiple bSSFP images were acquired with several different off-resonance angles. These images were combined in quadrature, resulting in a linear phase dependence to the off-resonance frequency, which can be used for thermometry measurements. Usually two to four images need to be acquired for a single temperature measurement.

It is with respect to these and other considerations that the various embodiments described below are presented.

SUMMARY

Some aspects of the present disclosure relate to systems and method for magnetic resonance (MR) thermometry using balanced steady state free precession (bSSFP). In some aspects, the present disclosure relates to systems and methods for accurately measuring and mapping the spatial distribution of temperature changes over time in aqueous media using magnetic resonance imaging. Some embodiments can utilize a PRF-based thermometry method, which collects temperature-sensitive phase images using a bSSFP pulse sequence, and the spatial distribution of temperature changes versus time in aqueous media can be mapped based on one, two, or three dimensional complex-valued MR images collected using a bSSFP pulse sequence.

Some embodiments can enable much greater sensitivity and speed than previous techniques for MR thermometry and thermography. Certain aspects of the present disclosure are particularly well-suited to MR thermometry and thermography of small, fast temperature changes over a region of limited spatial extent, as is commonly encountered during focused ultrasound procedures. Furthermore, by incorporating a feedback loop that can dynamically adjust the central frequency of the heightened sensitivity window in response to the measured temperature changes, some embodiments of the present disclosure permit the range of temperature changes that can be accurately measured to be expanded.

In one aspect, the present disclosure relates to a method for magnetic resonance thermometry which, in one embodiment, includes applying a preliminary bSSFP magnetic resonance imaging pulse sequence to an area of interest of a subject (also referred to herein as a "region of interest" of a subject). The preliminary bSSFP magnetic resonance imaging pulse sequence is configured for determining bSSFP image phases for a plurality of different frequencies within a predetermined range of frequencies that includes the resonance frequency associated with a target area that is within the area of interest. The method also includes determining, based on the determined bSSFP image phases, a relationship between the frequency and image phase associated with the area of interest and applying a bSSFP magnetic resonance imaging pulse sequence for temperature change measurement to the area of interest during and/or after focused energy is applied to the subject. The focused energy produces a temperature change in the target area, and the bSSFP magnetic resonance imaging pulse sequence is configured for determining an image phase change associated with the temperature change. The method also includes determining, based on the image phase change associated with the temperature change and using the determined relationship between the frequency and the image phase, a change in the resonance frequency associated with the target area due to the application of the focused energy and determining the temperature change based on the determined change in the resonance frequency.

The plurality of different frequencies may correspond to off-resonance frequencies defined by a difference between an actual resonance frequency associated with the target area and an operating frequency used for applying the preliminary bSSFP magnetic resonance imaging pulse sequence and/or the bSSFP magnetic resonance imaging pulse sequence for temperature change measurement.

The bSSFP magnetic resonance imaging pulse sequence for temperature change measurement may use an operating frequency determined based on the relationship between frequency and image phase associated with the area of interest determined using the preliminary bSSFP magnetic resonance imaging pulse sequence. Determining the relationship between the frequency and image phase associated with the area of interest may include measuring a phase transition curve.

In one embodiment, the method may also include, prior to applying the preliminary bSSFP magnetic resonance imaging pulse sequence and prior to the focused energy being applied to the subject, determining the predetermined range of frequencies by measuring resonance frequencies associated with the area of interest.

Determining the image phase change may include acquiring, using the bSSFP magnetic resonance imaging pulse sequence for temperature change measurement, a time series of images of the area of interest before, during, and/or after the application of the focused energy and correlating phase change to resonance frequency shift for one or more pixels of the time series of images. The change in resonance frequency may correspond to a proton resonance frequency (PRF) shift. The applied focused energy may include focused ultrasound and/or RF electromagnetic signals.

In one embodiment, the method may also include generating, based on the determined temperature change, one or more visual representations of the temperature associated with the target area before, during, and/or after the application of the focused energy. Generating the one or more visual representations may include generating one or more color maps showing temperature at a plurality of different locations proximate the target area at various points in time before, during, and/or after the application of the focused energy.

The predetermined range of frequencies may be set based on an expected range of temperatures to result from application of the focused energy to the target. In one embodiment, the method may also include controlling an operating parameter of a source of the focused energy, while the focused energy is being applied, based on the determined temperature change.

In one embodiment, the method may also include dynamically adjusting, during the application of the focused energy, an operating frequency used for the bSSFP magnetic resonance imaging pulse sequence for temperature change measurement based on the determined temperature change. Dynamically adjusting the operating frequency may include manipulating phases of RF pulses applied during the bSSFP magnetic resonance imaging pulse sequence for temperature change measurement. The temperature change may include heating and/or cooling of the target area. The target area may include biological tissue.

In another aspect, the present disclosure relates to a system for magnetic resonance thermometry. In one embodiment, the system includes a medical imaging device configured to apply a preliminary bSSFP magnetic resonance imaging pulse sequence to an area of interest of a subject. The preliminary bSSFP magnetic resonance imaging pulse sequence is configured for determining bSSFP image phase for a plurality of different frequencies within a predetermined range of frequencies that includes the resonance frequency associated with a target area that is within the area of interest. The system also includes one or more processors configured to determine, based on the determined bSSFP image phases, a relationship between the frequency and image phase associated with the area of interest. The system also includes a medical imaging device configured to apply a bSSFP magnetic resonance imaging pulse sequence for temperature change measurement to the area of interest during and/or after focused energy is applied to the subject from a source of focused energy. The focused energy produces a temperature change in the target area, and the bSSFP magnetic resonance imaging pulse sequence is configured for determining an image phase change associated with the temperature change. The one or more processors are further configured to determine, based on the image phase change associated with the temperature change, and using the determined relationship between the frequency and the image phase, a change in the resonance frequency associated with the target area due to the application of the focused energy, and determine the temperature change based on the determined change in the resonance frequency.

The plurality of different frequencies may correspond to off-resonance frequencies defined by a difference between an actual resonance frequency associated with the target area and an operating frequency used by the medical imaging device for applying the preliminary bSSFP magnetic resonance imaging pulse sequence and/or the bSSFP magnetic resonance imaging pulse sequence used by the medical imaging device for temperature change measurement.

The bSSFP magnetic resonance imaging pulse sequence for temperature change measurement may use an operating frequency determined based on the relationship between frequency and image phase associated with the area of interest determined using the preliminary bSSFP magnetic resonance imaging pulse sequence. Determining the relationship between the frequency and image phase associated with the area of interest may include measuring a phase transition curve.

The one or more processors may also be configured to, prior to applying the preliminary bSSFP magnetic resonance imaging pulse sequence and prior to the focused energy being applied to the subject, determine the predetermined range of frequencies by measuring resonance frequencies associated with the area of interest.

Determining the image phase change may include acquiring, using the bSSFP imaging pulse sequence, a time series of images of the area of interest before, during, and/or after the application of the focused energy and correlating phase change to resonance frequency shift for one or more pixels of the time series of images. The change in resonance frequency may correspond to a proton resonance frequency (PRF) shift. The applied focused energy may include focused ultrasound and/or RF electromagnetic signals.

The one or more processors may also be configured to generate, based on the temperature change, one or more visual representations of the temperature associated with the target before, during, and/or after the application of the focused energy. Generating the one or more visual representations may include generating one or more color maps showing temperature at a plurality of different locations proximate the target area at various points in time before, during, and/or after the application of the focused energy.

The predetermined range of frequencies may be set based on an expected range of temperatures that will result from application of the focused energy to the target. The one or more processors may also be configured to control an operating parameter of a source of the focused energy, while the focused energy is being applied, based on the determined temperature change.

The one or more processors may also be configured to dynamically adjust an operating frequency used for the bSSFP magnetic resonance imaging pulse sequence during the application of the focused energy, based on the determined temperature change. Dynamically adjusting the operating frequency may include manipulating phases of RF pulses applied during the bSSFP magnetic resonance imaging pulse sequence.

The temperature change may include heating and/or cooling of the target area. The target area may include biological tissue. The medical imaging device for applying the preliminary bSSFP magnetic resonance imaging pulse sequence and the medical imaging device for applying the bSSFP magnetic resonance imaging pulse sequence for temperature change measurement may be the same medical imaging device or different medical imaging devices.

In another aspect, the present disclosure relates to a method which, in one embodiment, includes, responsive to a preliminary balanced bSSFP magnetic resonance imaging pulse sequence being applied to an area of interest of a subject, the preliminary bSSFP magnetic resonance imaging pulse sequence being configured for determining bSSFP image phase for a plurality of different frequencies within a predetermined range of frequencies, and wherein the predetermined range of frequencies includes the resonance frequency associated with a target area that is within the area of interest, determining, based on the determined bSSFP image phases, a relationship between the frequency and image phase associated with the area of interest. The method also includes, responsive to a bSSFP magnetic resonance imaging pulse sequence for temperature change measurement being applied to the area of interest during and/or after focused energy is applied to the subject, wherein the focused energy produces a temperature change in the target area, and the bSSFP magnetic resonance imaging pulse sequence is configured for determining an image phase change associated with the temperature change, determining, based on the image phase change associated with the temperature change and using the determined relationship between the frequency and the image phase, a change in the resonance frequency associated with the target area due to the application of the focused energy. The method also includes determining the temperature change based on the determined change in the resonance frequency.

The plurality of different frequencies may correspond to off-resonance frequencies defined by a difference between an actual resonance frequency associated with the target area and an operating frequency used for applying the preliminary bSSFP magnetic resonance imaging pulse sequence and/or the bSSFP magnetic resonance imaging pulse sequence for temperature change measurement.

The bSSFP magnetic resonance imaging pulse sequence for temperature change measurement may use an operating frequency determined based on the relationship between frequency and image phase associated with the area of interest determined using the preliminary bSSFP magnetic resonance imaging pulse sequence. Determining the relationship between the frequency and image phase associated with the area of interest may include measuring a phase transition curve.

The method may also include, prior to the preliminary bSSFP magnetic resonance imaging pulse sequence being applied and prior to the focused energy being applied to the subject, determining the predetermined range of frequencies by measuring resonance frequencies associated with the area of interest. Determining the image phase change may include acquiring, using the bSSFP magnetic resonance imaging pulse sequence for temperature change measurement, a time series of images of the area of interest before, during, and/or after the application of the focused energy and correlating phase change to resonance frequency shift for one or more pixels of the time series of images. The change in resonance frequency may correspond to a proton resonance frequency (PRF) shift. The applied focused energy may include focused ultrasound and/or and RF electromagnetic signals.

The method may also include generating, based on the determined temperature change, one or more visual representations of the temperature associated with the target area before, during, and/or after the application of the focused energy. Generating the one or more visual representations may include generating one or more color maps showing temperature at a plurality of different locations proximate the target area at various points in time before, during, and/or after the application of the focused energy. The predetermined range of frequencies may be set based on an expected range of temperatures to result from application of the focused energy to the target.

The method may also include controlling an operating parameter of a source of the focused energy, while the focused energy is being applied, based on the determined temperature change. The method may also include dynamically adjusting, during the application of the focused energy, an operating frequency used for the bSSFP magnetic resonance imaging pulse sequence for temperature change measurement based on the determined temperature change. Dynamically adjusting the operating frequency may include manipulating phases of RF pulses applied during the bSSFP magnetic resonance imaging pulse sequence for temperature change measurement. The temperature change may include heating and/or cooling of the target area. The target area may include biological tissue.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Figure 1:
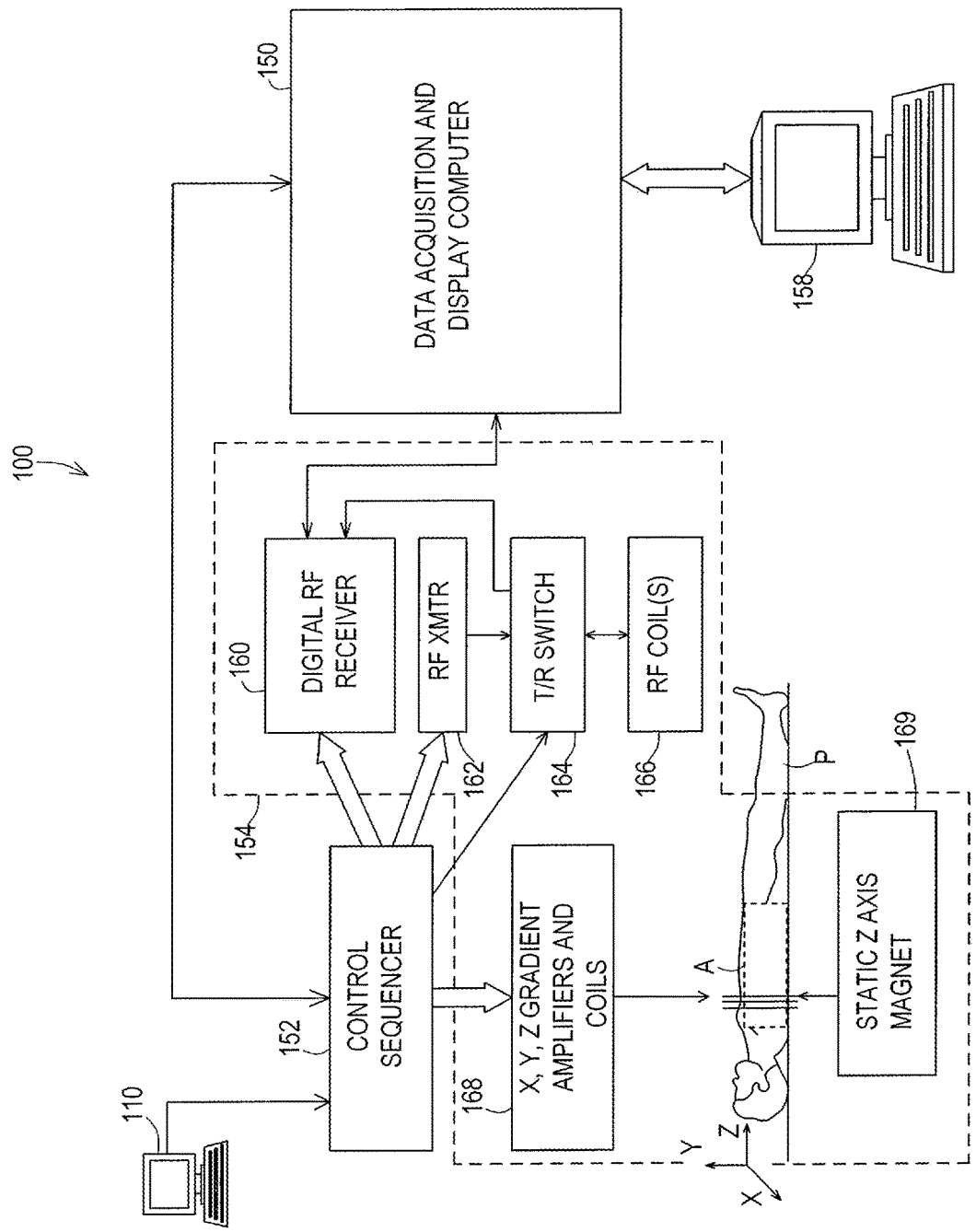
FIG. 1 is a system diagram illustrating an imaging system capable of implementing aspects of the present disclosure in accordance with one or more embodiments.

Some aspects of the present disclosure relate to systems and methods for magnetic resonance (MR) thermometry using balanced steady state free precession (bSSFP). Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

An overview of some objectives and example embodiments and implementations of the present disclosure will now be provided, as well as discussion of various aspects of the present disclosure in comparison to conventional systems and methods for magnetic resonance thermometry.

In some aspects, the present disclosure relates to PRF shift thermometry methods and systems based on a bSSFP pulse sequence, which makes direct use of the sharp phase change near resonance to quantify temperature changes in aqueous media (such as biological tissue, for example human tissue). This approach features high sensitivity to small temperature changes and enables much better temporal resolution than previous techniques. Among other applications, certain embodiments of the present disclosure are useful in applications for which the temperature changes one is interested in measuring are relatively small (<10° C.) and/or fast. One such application is locating or characterizing the shape of the focal spot during focused ultrasound procedures, without inducing significant tissue heating, by applying a brief, low energy sonication pulse. Another such application is monitoring temperature changes in areas surrounding the most intense focal region, to carefully monitor thermal dose delivered to healthy tissue outside the intended target.

Because the implementation of some embodiments of the present disclosure enable high temporal resolution, they are also useful for cases where rapid temperature feedback is desirable. For instance, some embodiments can be used to enhance the safety of MR-guided focused ultrasound procedures, by closely monitoring undesired heating of healthy tissue in near-real time and triggering power cutoff at a predetermined safety threshold.

Figure 5:
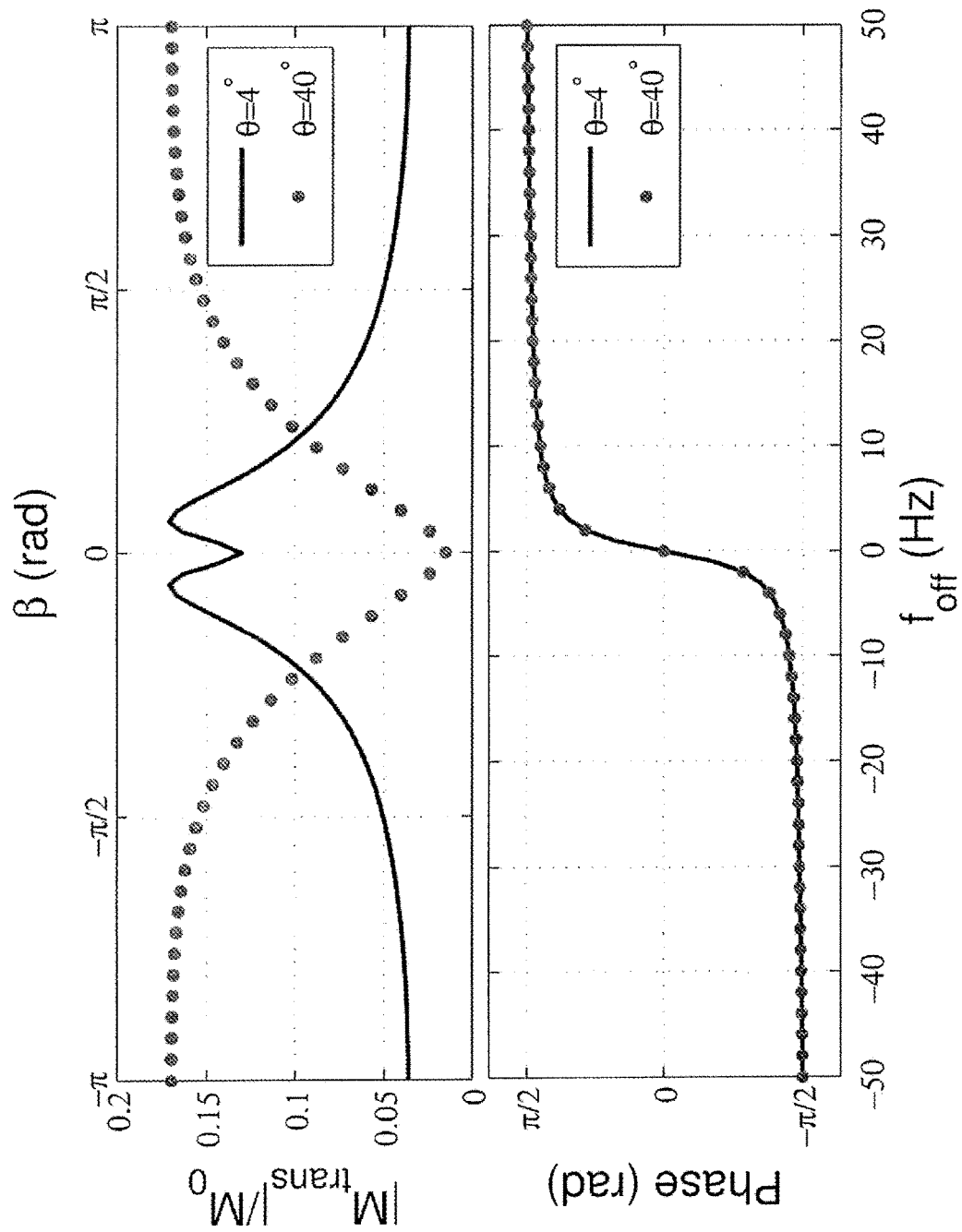
FIG. 5 shows the theoretical magnitude and phase at TE=TR/2 of the bSSFP signal, for two different flip angles, assuming typical values of T1, T2, and TR.
Figure 6:
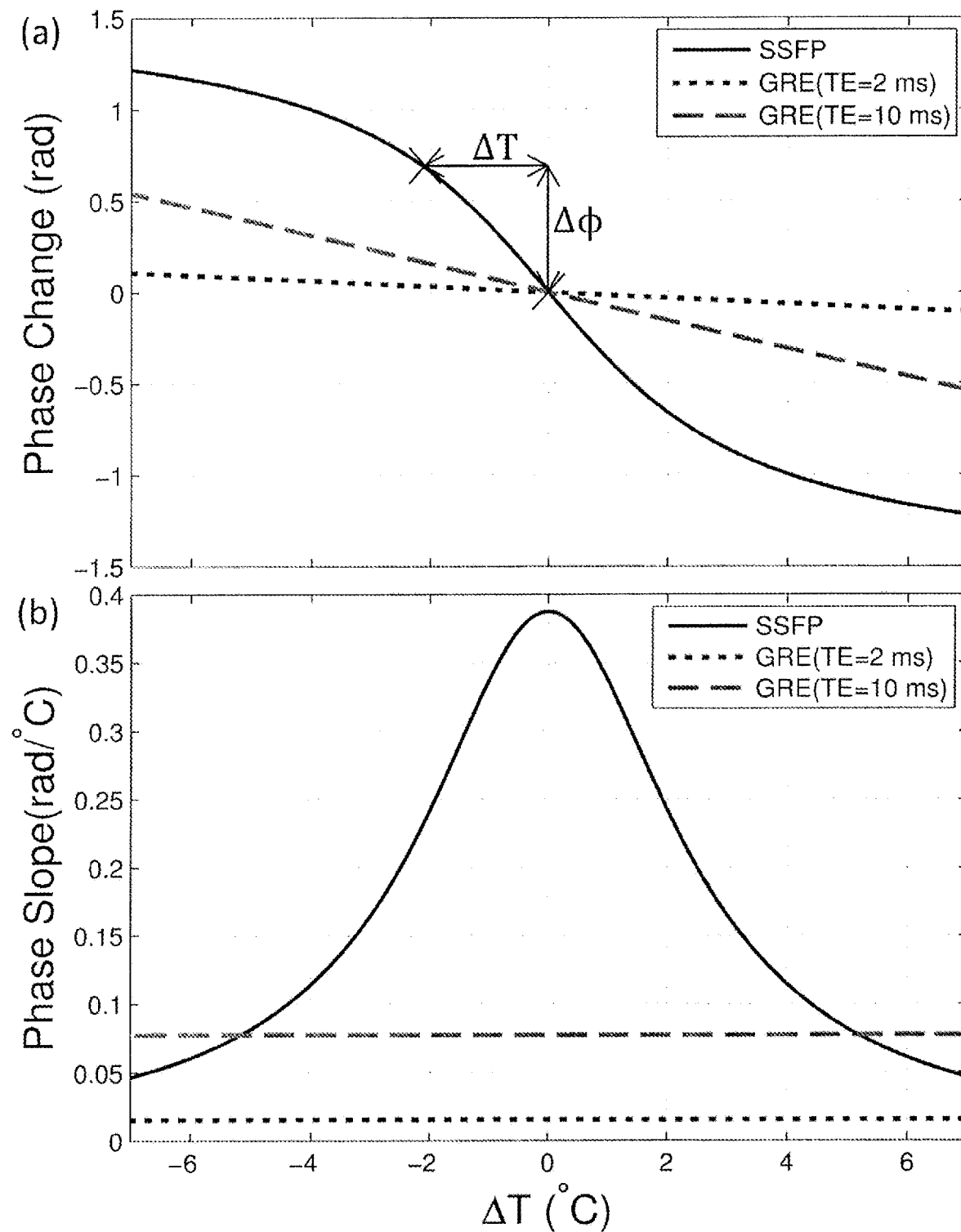
FIG. 6 shows sample plots of image phase versus temperature change for bSSFP and GRE image acquisitions and slope of the phase change curve, according to an embodiment of the present disclosure.

In comparison to other conventional MR thermometry techniques discussed above, such as those relying on GRE, MR thermometry using a bSSFP pulse sequence can enable much greater sensitivity and speed by making use of the sharp phase transition illustrated in the bottom graph of FIG. 5. The theoretical slope of the bSSFP phase-versus-frequency curve is given by:

$$\frac{d\phi}{d(\Delta f)} = \pi TR \frac{E_2^{-2} - 1}{1 + E_2^{-2} - 2E_2^{-1}\cos(2\pi \Delta f TR)}. \quad [\text{Eq. 2}]$$

where the off-resonance frequency $\Delta f$ is defined to be the difference between the scanner operating frequency and the actual Larmor frequency, $E_2 = e^{-TR/T2}$, and $\beta = 2\pi\Delta f TR$ is the total phase angle accrued between two adjacent RF pulses, often referred to as the off-resonance phase angle. Eq. 2 can be calculated from well-known expressions for the bSSFP signal, such as those given in reference [5]. It is noteworthy that the phase-frequency relationship in Eq. 2 is independent of both the flip angle and T1.

This expression for the slope can be expanded as a Taylor series in $\Delta f$. Under the assumption that $TR \ll T_2$, the Taylor series can be written:

$$\frac{d\phi}{d(\Delta f)} = 2\pi T_2 - 8\pi T_2^3 T \Delta f^2 + O(\Delta f^4), \quad [\text{Eq. 3}]$$

In this regime, the slope at $\Delta f=0$ is simply $2\pi T_2$, which means that the slope is independent of TE and TR. Thus the time required to obtain a single image (and therefore the temporal resolution of the measurement) can be improved by shortening TE and TR, without compromising the temperature sensitivity. Small temperature changes near resonance are related to bSSFP phase changes by:

$$\Delta T = \frac{\Delta \phi}{\alpha \gamma \beta_0 T_2}, \quad [\text{Eq. 4}]$$

which suggests a higher temperature sensitivity than GRE PRF thermometry (given in Eq. 1), since $T_2$ is usually much larger than TE.

Unlike the spoiled GRE case, the bSSFP image phase does not depend on the temperature linearly over a wide temperature range. While in theory the phase of the bSSFP images can be mapped to PRF (and thus temperature) as long as T2 and the initial off-resonance frequency are known, in practice T2 is not well known. Also, the actual relationship between image phase and resonant frequency may be more complicated than the theoretical relationship given in Eq. 2 and may generally differ from pixel to pixel across the region of interest.

According to some embodiments of the present disclosure, the phase-frequency relationship is measured in situ on a pixel-by-pixel basis as part of the thermometry procedure, in order to accurately map image phase to temperature during the quantitative analysis. This step can significantly enhance the quantitative accuracy and overall robustness of our thermometry method.

Although some thermometry techniques based on a bSSFP pulse sequence have been developed previously, aspects of the present disclosure presented herein differ significantly and provide advantages and benefits over the prior techniques. In one known bSSFP thermometry technique ([6]), multiple magnitude MR images are collected by varying the phase addition of each RF pulse (which is equivalent to changing the RF frequency), and the PRF can be determined by analyzing the relative signal magnitudes across the group of images. Another set of images is collected later during the heating procedure, and a new PRF frequency can be similarly determined. The temperature change is then calculated based on the PRF change, like all other PRF-based thermometry techniques. In contrast to this technique ([6]), thermometry techniques according to some embodiments of the present disclosure make exclusive use of the phase, not magnitude, of the bSSFP images, and they can be significantly more time-efficient. Furthermore, techniques in accordance with some embodiments of the present disclosure require only a single image at each time point to update the temperature map. Because the technique of reference [6] may require multiple images to analyze the PRF shift, the temporal resolution of this technique may be worse than the GRE-based methods.

Unlike prior bSSFP MR thermometry techniques, in which multiple images need to be collected at a given time point to determine the temperature change since a previous time point, in techniques in accordance with some embodiments of the present disclosure each new complex-valued image can be converted to an updated temperature map. Embodiments of the present disclosure can enable much higher sensitivity and speed than GRE-based thermometry. This increase in sensitivity and speed can be accomplished by making direct use of the sharp phase transition that occurs over a narrow range of off-resonance frequencies for a bSSFP imaging pulse sequence. Rather than relying on the theoretical shape of this phase transition curve to map phase change to temperature change, in accordance with some embodiments of the present disclosure the phase transition curve is directly measured in a separate pre-scan, by manipulating the frequency and/or phase of the excitation RF pulses. Because the phase transition curve is highly nonlinear and its exact shape will generally vary depending on the exact tissue composition, measuring this curve in situ substantially enhances the quantitative accuracy and general robustness of our thermometry technique. Because this part of the process can be performed completely separately from the main thermometry scan, it does not compromise the temporal resolution of the main thermometry scan.

A further detailed description of aspects of the present disclosure will now be provided with reference to the accompanying drawings. The drawings form a part hereof and show, by way of illustration, specific embodiments or examples. In referring to the drawings, like numerals represent like elements throughout the several figures.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged. A contrast-enhanced image of an area of interest A of the subject P (which may also be referred to herein as a "region of interest") may be shown on display 158. The display 158 may be implemented through a variety of output interfaces, including a monitor, printer, or data storage.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
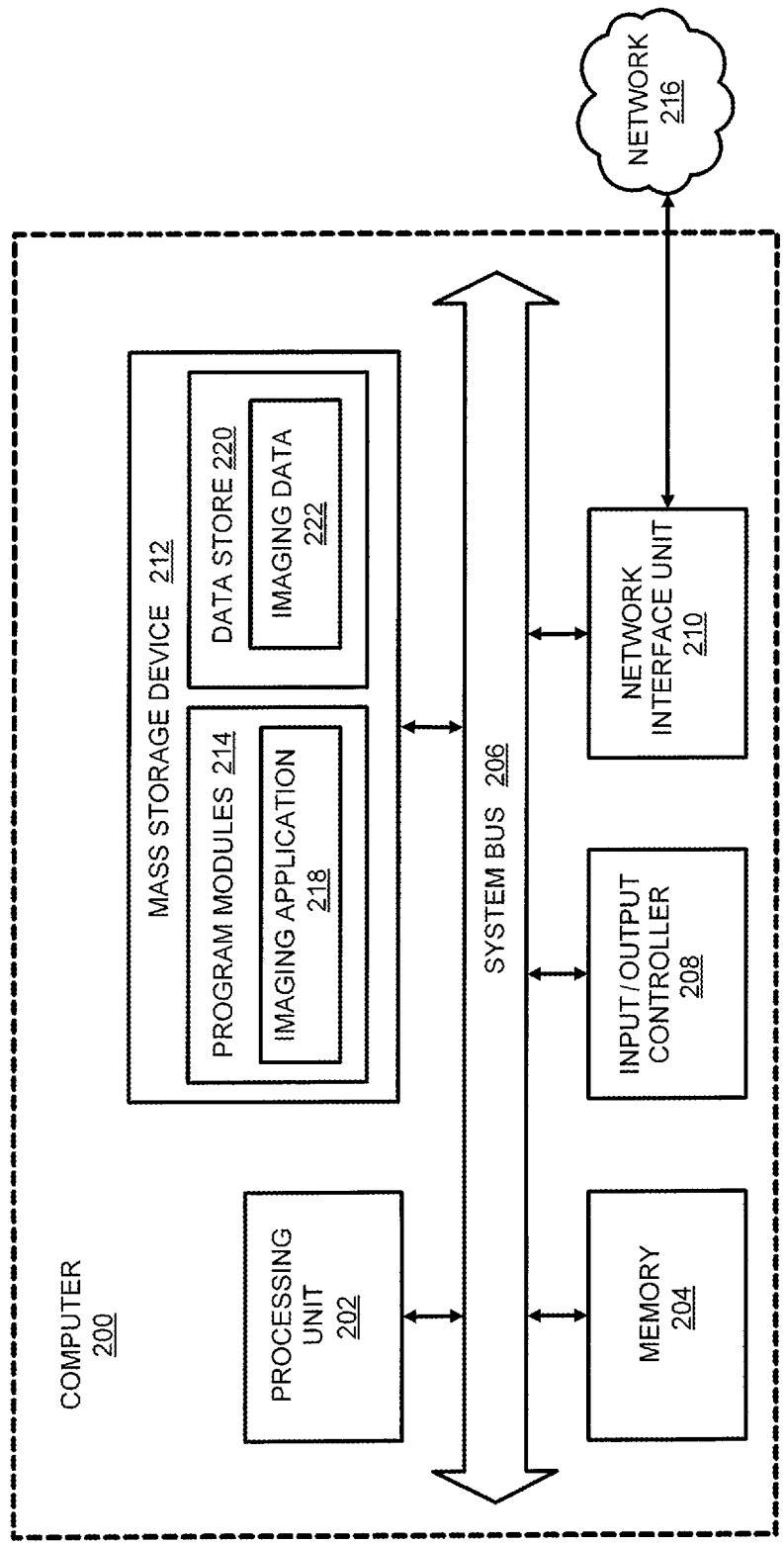
FIG. 2 is a computer architecture diagram showing a general computing system capable of implementing aspects of the present disclosure in accordance with one or more embodiments.

FIG. 2 is a computer architecture diagram showing a general computing system capable of implementing aspects of the present disclosure in accordance with one or more embodiments described herein. A computer 200 may be configured to perform one or more functions associated with embodiments illustrated in one or more of FIGS. 3-12. For example, the computer 200 may be configured to perform operations of the method shown in FIG. 3. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of FIGS. 3-12 discussed below, for example to cause the computer 200 to perform operations of the method shown in FIG. 3. The program modules 214 may include an imaging application 218 for performing data acquisition and/or processing functions as described herein, for example to acquire and/or process image data corresponding to magnetic resonance imaging of an area of interest. The imaging application 218 may further be configured and executable for performing control operations for feedback-based management of operating parameters of various medical imaging devices and/or sources of focused energy for heating or cooling tissue as described herein. The computer 200 can include a data store 220 for storing data that may include imaging-related data 222 such as acquired image data from the implementation of magnetic resonance imaging pulse sequences in accordance with various embodiments of the present disclosure, or temperature-location based visual representations such as maps generated in accordance with various embodiments of the present disclosure described herein.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a BLUETOOTH® enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more embodiments illustrated in FIGS. 3-12. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202. Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Figure 3:
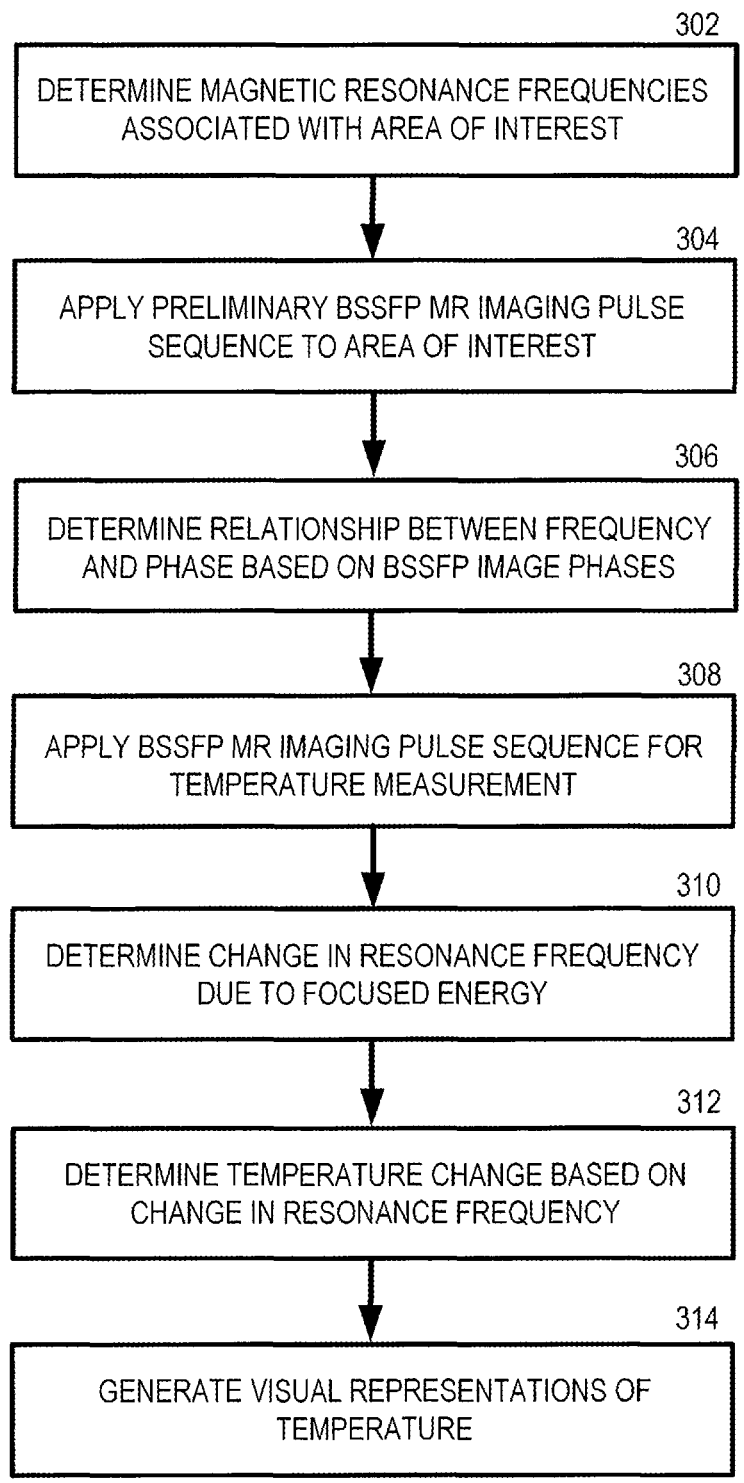
FIG. 3 is a flow diagram illustrating operations of a method for magnetic resonance thermometry according to one embodiment of the present disclosure.

FIG. 3 is a flow diagram illustrating operations of a method 300 for magnetic resonance thermometry, according to one embodiment of the present disclosure. As shown, at 302, a range of magnetic resonance frequencies associated with an area of interest of a subject is determined. At 304, a preliminary bSSFP magnetic resonance imaging sequence is applied to the area of interest of the subject. The bSSFP magnetic resonance imaging sequence is configured for determining bSSFP image phase for a plurality of different frequencies within the range of frequencies determined at 302, which include the resonance frequency associated with a target area that is within the area of interest. At 306, a relationship between the frequency and image phase associated with the area of interest is determined based on the determined bSSFP image phases.

At 308, a bSSFP magnetic resonance imaging pulse sequence for temperature change measurement is applied to the area of interest during and/or after focused energy is applied to the subject, where the focused energy produces a temperature change in the target area. The bSSFP magnetic resonance imaging pulse sequence is configured for determining an image phase change associated with the temperature change. At 310, based on the image phase change associated with the temperature change, and using the relationship between the frequency and the image phase determined at 306, a change in the resonance frequency associated with the target area due to the application of the focused energy is determined. At 312, the temperature change is determined based on the change in the resonance frequency determined at 310. At 314, one or more visual representations are generated, of the temperature associated with the target area before, during and/or after the application of the focused energy.

The method 300 may also include controlling an operating parameter of a source of the focused energy, while the focused energy is being applied, based on the determined temperature change. The method 300 may also include dynamically adjusting, during the application of the focused energy, an operating frequency used for the bSSFP magnetic resonance imaging pulse sequence for temperature change measurement, based on the determined temperature change.

Balanced Steady-State Free Precession

Figure 4:
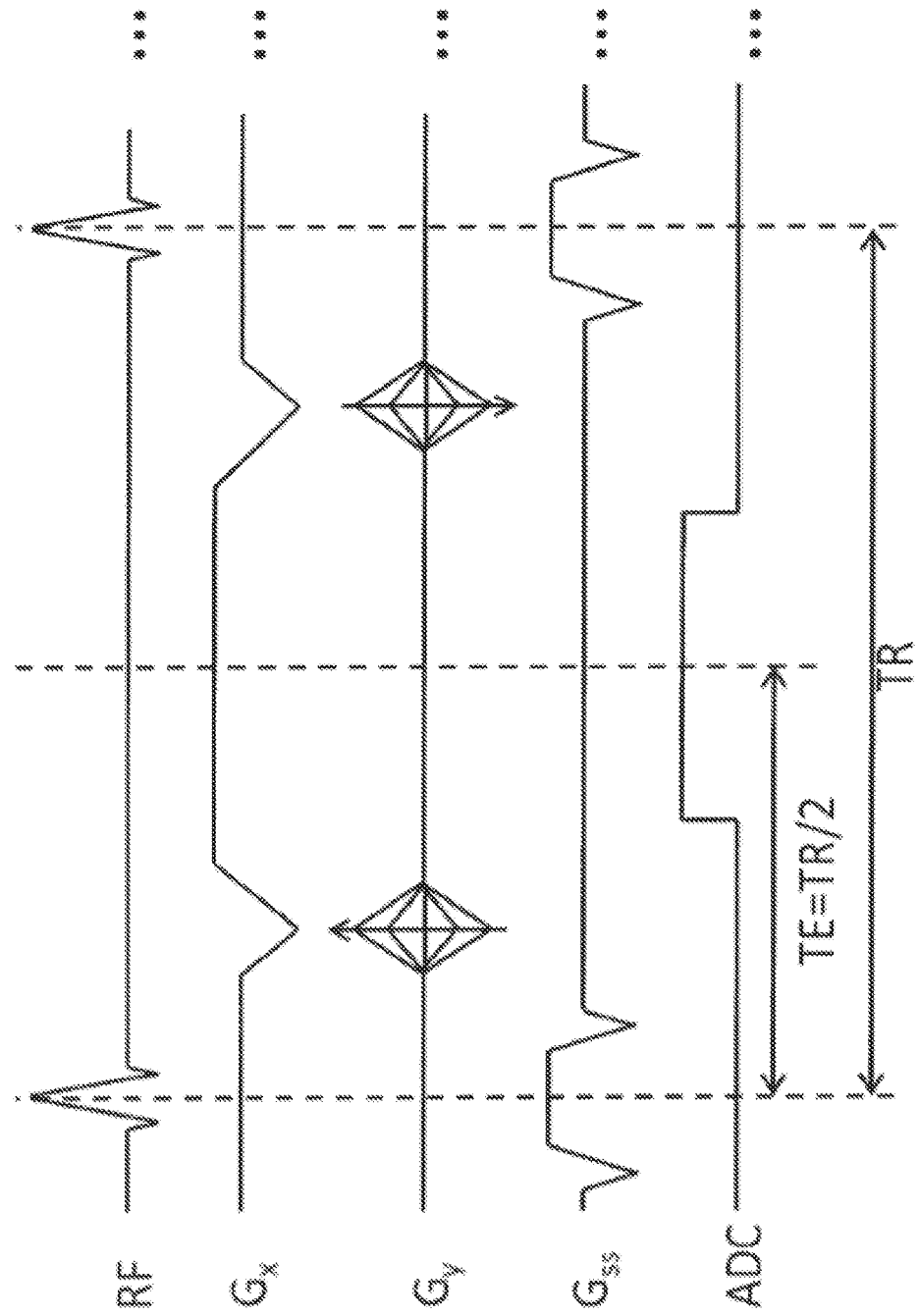
FIG. 4 is a pulse sequence diagram of a generic balanced steady-state precession (bSSFP) pulse sequence for magnetic resonance imaging, which may be utilized to implement certain aspects of the present disclosure.

FIG. 4 depicts a pulse sequence diagram of a generic bSSFP pulse sequence for magnetic resonance imaging, which may be utilized to implement certain aspects of the present disclosure. The pulse sequence comprises a train of identical RF pulses separated by a constant repetition time TR that is short compared to the spin relaxation times T1 and T2. Imaging gradient pulses are executed during the time between RF pulses, just as in any MRI pulse sequence; however, all gradients are "balanced," which means that all gradient moments are rewound before the next RF pulse, so that the net gradient moment along any direction is zero during every TR period ([7]).

Under these conditions, the phase accrued by the transverse magnetization during each TR period is constant at a given spatial location, and is proportional to the product of the repetition time TR and the difference between the nominal scanner frequency setting and the actual magnetic resonance frequency at the given spatial location. This accrued phase may be referred to as the "off-resonance phase" and represented mathematically by the symbol $\beta$. Furthermore, both the transverse and longitudinal components of the magnetization remaining at the end of each TR period contributes to the transverse magnetization in the next TR period, which leads to a steady-state MR signal. This complex-valued signal depends on the off-resonance phase, the flip angle of the RF pulse, and the relaxation times T1 and T2 ([5]).

The theoretical bSSFP signal magnitude and phase are plotted versus off-resonance phase β in FIG. 5, for typical values of T1, T2, and flip angle. These plots illustrate two features of the bSSFP signal. First, the signal magnitude tends to be large near resonance (β=0°) for small flip angles, but large away from resonance (β=±180°) for large flip angles. Second, the signal phase at TE=TR/2 is nearly independent of β over a wide range of values but undergoes a sharp transition at β=0°. This sharp transition may be used in MR thermometry methods in accordance with certain aspects of the present disclosure.

Proton Resonance Frequency (PRF) Temperature Shift

It is established that the magnetic resonance frequency of the hydrogen nuclei in water molecules depends roughly linearly on temperature over a wide range of temperatures, with coefficient of proportionality α=−0.01 ppm/° C. Thus by measuring changes in the resonance frequency during heating or cooling, the temperature change of aqueous media (such as water-containing tissues in the human body) may be quantified using this relationship. This is the basic principle behind all PRF-based MR thermometry techniques.

MR Thermometry Using a GRE Pulse Sequence

Spoiled gradient-recalled-echo (GRE) pulse sequences are typically used to perform PRF-based MR thermometry during thermal treatments ([1],[2]), because they provide straightforward and robust sensitivity to the PRF shift. For a spoiled GRE imaging pulse sequence, the relationship between the image phase (φ) and resonance frequency shift (Δf) is given by φ=2πΔfTE, where TE is the echo time. Thus when such a pulse sequence is used to measure a frequency shift (for instance, one caused by a temperature change), the sensitivity of the measurement is proportional to the echo time TE. The graph in FIG. 6(a) shows the relationship between temperature and image phase for a GRE pulse sequence at two different echo times, according to an embodiment of the present disclosure. The slope of the line (and thus the sensitivity of the measurement) is greater for the longer echo time. As shown, the relationship between image phase and temperature is nonlinear for the bSSFP case.

MR Thermometry Using a bSSFP Pulse Sequence

For comparison with the GRE case, the relationship between image phase and temperature for a bSSFP pulse sequence is also shown in FIG. 6(a). FIG. 6(b) shows a plot of the slopes of the curves in FIG. 6(a). Here, it was assumed that T2=50 ms for the bSSFP acquisition and TE=2 ms and 10 ms for the GRE cases. Within a temperature range +/−5° C., the bSSFP thermometry acquisition is more sensitive than a GRE acquisition with TE=10 ms. The slope of the bSSFP curve is much greater for a range of off-resonance frequencies around β=0°, which means that the bSSFP image phase is much more sensitive to temperature changes in this range. This range of frequencies may be referred to herein as the "window of heightened sensitivity."

In some embodiments of the present disclosure, an abrupt phase transition may occur in the vicinity of the region of interest. The relationship between image phase and resonant frequency is nonlinear in this vicinity, which presents a challenge for temperature quantification. In some embodiments, a preparatory scan is performed to directly map out this phase transition over the region of interest, to allow the frequency to be adjusted to ensure maximum sensitivity over this region and to allow accurate quantitative mapping of phase to temperature.

Expanding the Temperature Range Accessible by the bSSFP Method

According to some embodiments of the present disclosure, the range of temperature changes that can be accurately and sensitively measured using bSSFP-based methods is restricted to a relatively narrow range (on the order of 10° C. wide), corresponding to the range of frequencies spanning the window of heightened sensitivity. By centering this window about a predetermined setpoint $T_{set}$, temperatures within a relatively narrow range about $T_{set}$ may be accurately measured. The range of temperature changes that can be accurately measured using the core bSSFP technique during a single measurement can be expanded by incorporating a feedback loop into the system, that dynamically shifts the center frequency of the window of heightened sensitivity during heating/cooling, by adjusting the effective operating frequency of the scanner.

In some embodiments of the present disclosure, the effective operating frequency is adjusted before each new image acquisition by an amount determined based on previously acquired images, in order to follow the changing resonant frequency at the location of heating, to thereby keep the off-resonance frequency difference small from one frame to the next, so that high temperature sensitivity is achieved for every temporal frame, regardless of the amount of total temperature change that has occurred since the beginning of the scan. For each frame (herein numbered sequentially using the variable n), an off-resonance frequency difference Δfn between the current frame and the previous frame is extracted, and also, how much the scanner frequency has been shifted since the beginning of the scan can be tracked, which may herein referred to as fn. The temperature in the nth frame can then be accurately determined by $$\Delta T_n = 2\pi(f_{n2} - f_{n1} + \Delta f_n)/(\alpha \gamma B_0)$$ [Eq. 5]

Acoustic Radiation Force Imaging (ARFI) Using a bSSFP Pulse Sequence

According to some aspects of the present disclosure, similar principles can also be applied to enable high speed, high sensitivity MR acoustic radiation force imaging (MR ARFI). By inserting displacement encoding gradients into the bSSFP sequence and properly synchronizing bursts of focused ultrasound, an off-resonance phase angle can be generated at the ultrasound focus, leading to a much larger change in the image phase than existing MR ARFI techniques ([8]) due to the amplification of off-resonance phase in the vicinity of the bSSFP phase transition.

A method for MR thermometry in accordance with an embodiment of the present disclosure will now be described with reference to its various operational steps. In a first step, a subject is positioned in an MR scanner and MR images are acquired to locate a region of interest containing an expected heating spot. For instance, the expected heating spot may be the focal spot of a focused ultrasound transducer, whose general location can usually be predicted based on prior knowledge. In a second step, a coarse-step frequency-mapping MRI scan is performed to determine the approximate resonance frequency and its range of variation over the region of interest. Set the scanner operating frequency to a value within this range. This step can be optional, because the necessary information may be gleaned from the third step described below, but this optional second step may in some implementations help reduce the frequency range that needs to be scanned in the third step.

In a third step, a series of fine-step preparatory bSSFP scans are performed over the region of interest, in order to calibrate the mapping between the scanner operating frequency and the phase of the resulting complex-valued MR images. These scans yield a series of complex-valued images, each of which is obtained at a different effective resonance frequency. The range and spacing of the measured effective frequencies is designed to sample a frequency range spanning the sharp bSSFP phase transition (the window of heightened sensitivity) over the region of interest. These images are then analyzed on a pixel-by-pixel basis to determine the exact frequency offset and shape of the frequency-sensitive bSSFP phase transition at each pixel location in the region of interest of the subject.

For the purposes of this preparatory step, variation of the effective frequency can be achieved in more than one way, including one of the following ways: (a) perform separate scans at each desired frequency setting, and actually change the scanner operating frequency to the new value between scans; or (b) leave the scanner operating frequency at the same value, but mimic a frequency change $\Delta f$ by increasing the phase of the excitation RF pulse by an amount TR $\Delta f$ from one pulse to the next within each image acquisition. To maintain a consistent phase in the acquired signal, its complex phase should also be increased by an additional amount TR $\Delta f/2$ (for TE=TR/2). For some MR scanners, this method of varying the effective frequency may be more convenient for automating the frequency-scanning procedure, as it allows the whole procedure, which acquires multiple phase images at a range of off-resonance frequencies $\Delta f$, to be easily combined into a single scan. It should be recognized that although the bSSFP thermometry method of reference [6] changes the "resonance frequency offset" using similar means, it is used in reference [6] to determine bSSFP image magnitude changes, in contrast to mapping bSSFP image phase changes in accordance with certain embodiments of the present disclosure.

In a fourth step, information obtained in the third step can be used to choose a suitable operating frequency setting for the time-dependent temperature measurement to be performed in a fifth step described below. An objective of the fourth step is to ensure that the bSSFP phase transition (window of heightened sensitivity) occurs at the location of interest. It may be desirable to use a frequency setting different from the initial resonant frequency at the expected location of focal heating (for example, near one edge of the window of heightened sensitivity), so that the phase starts out nonzero but passes through zero during heating, in order to make good use of the limited dynamic range of the bSSFP phase transition. Or, it may be desirable to use a frequency setting that is well outside the window of heightened sensitivity, in order to center this window at a frequency that corresponds to a predetermined, relatively large temperature change $T_{set}-T_{start}$. In this case the image phase would not change appreciably until the temperature nears the predetermined setpoint $T_{set}$, and therefore the measured temperature changes would be most accurate over a relatively narrow range of temperatures centered on $T_{set}$.

In a fifth step, a time series of one, two, or three dimensional bSSFP images are acquired of the same region of interest, using the frequency setting chosen in the fourth step, while the region of interest is being heated (for example by application of focused ultrasound) or cooled (for example by ceasing the application of focused ultrasound, in which case the added heat will begin dissipating). The frequency setting chosen under the fourth step can be implemented in practice either by actually changing the operating frequency to the desired value before the acquisition of the time series, or by incrementing the phase of the RF pulse, as described in step 3b.

In a sixth step, the phase-to-frequency mapping measured in the third step is used to convert the phase change at each image pixel to a frequency change, and the corresponding temperature change between any two images is calculated using the known relationship: $\Delta T=2\pi\Delta f/(\alpha\gamma B_0)$, where $\alpha=-0.01$ ppm/° C. is the PRF temperature coefficient for aqueous tissue, y is the gyromagnetic ratio (in radians per Tesla), and $B_0$ is the holding field.

The following description provides a further discussion of certain aspects of the present disclosure in accordance with example embodiments. A description of example implementations and results of practicing various aspects of the present disclosure will be presented.

Example Implementations and Results

Various aspects of the present disclosure may be still more fully understood from the following description of some example implementations and corresponding results and the images of FIGS. 7-12. Some experimental data are presented herein for purposes of illustration and should not be construed as limiting the scope of the present disclosure in any way or excluding any alternative or additional embodiments.

Example 1

Figure 7:
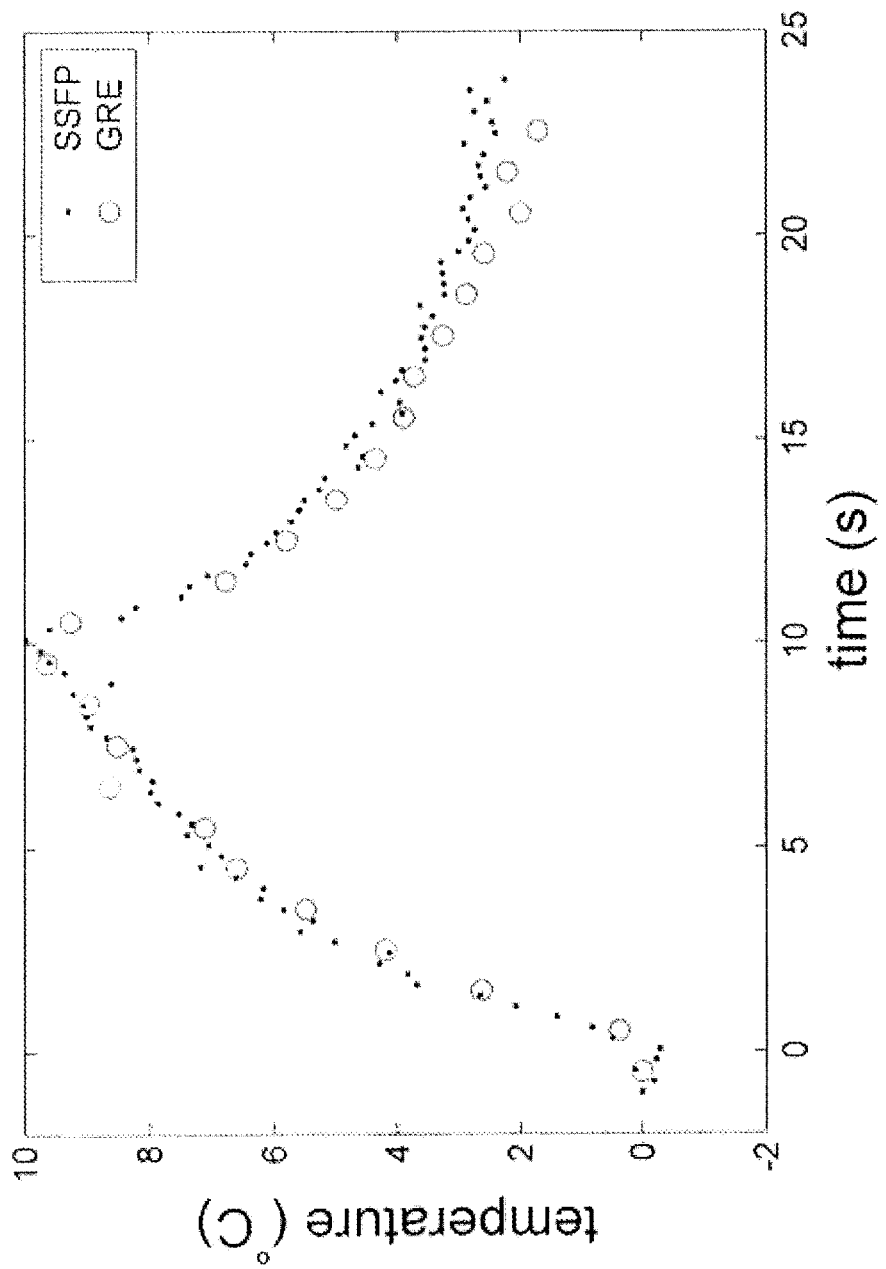
FIG. 7 illustrates slow temperature change measured with GRE and bSSFP pulse sequences, in accordance with an example implementation of some aspects of the present disclosure that is also referred to herein as "Example 1".
Figure 8:
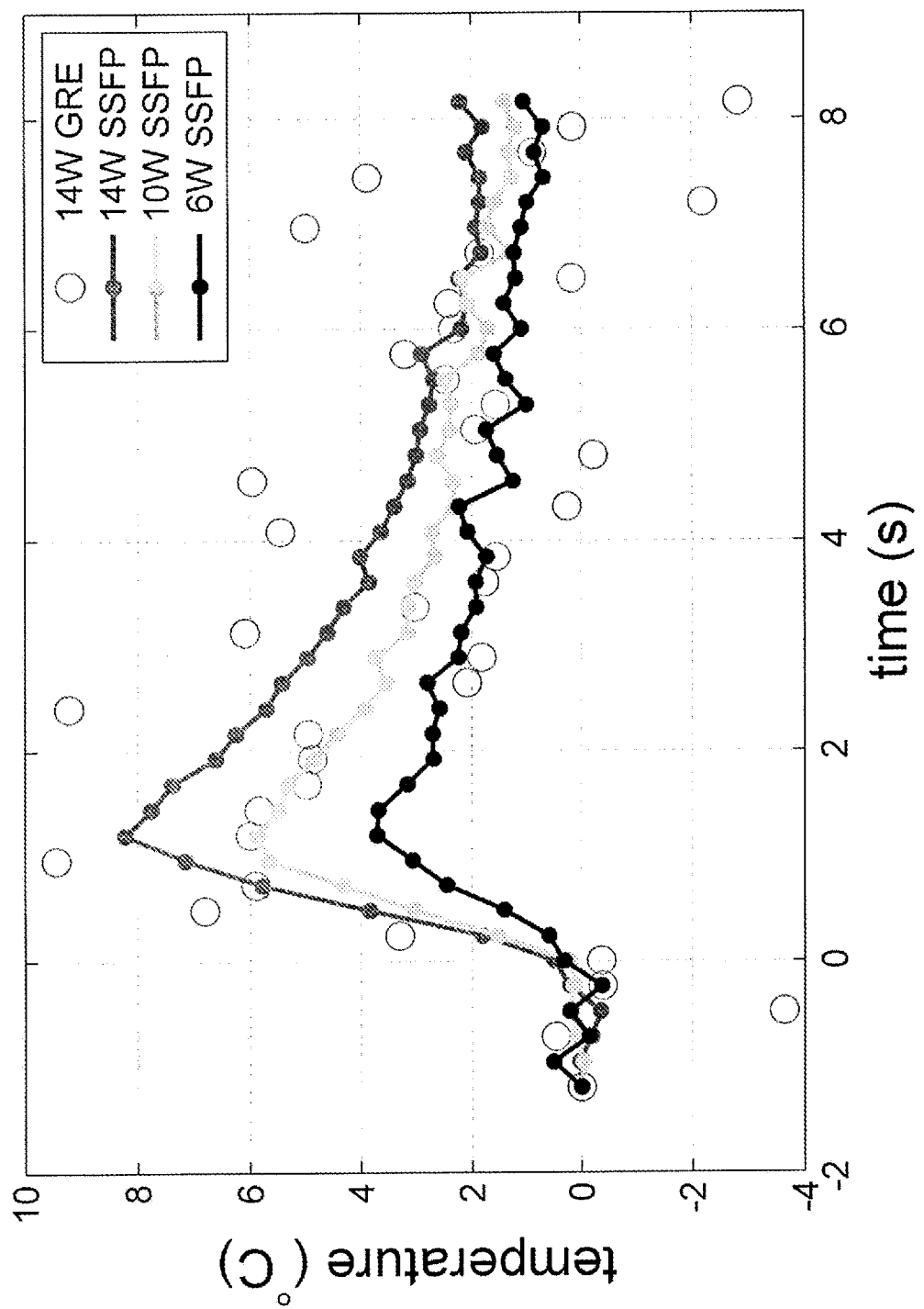
FIG. 8 illustrates, with respect to Example 1, temperature evolution during fast temperature change measured with GRE and bSSFP pulse sequences.
Figure 9:
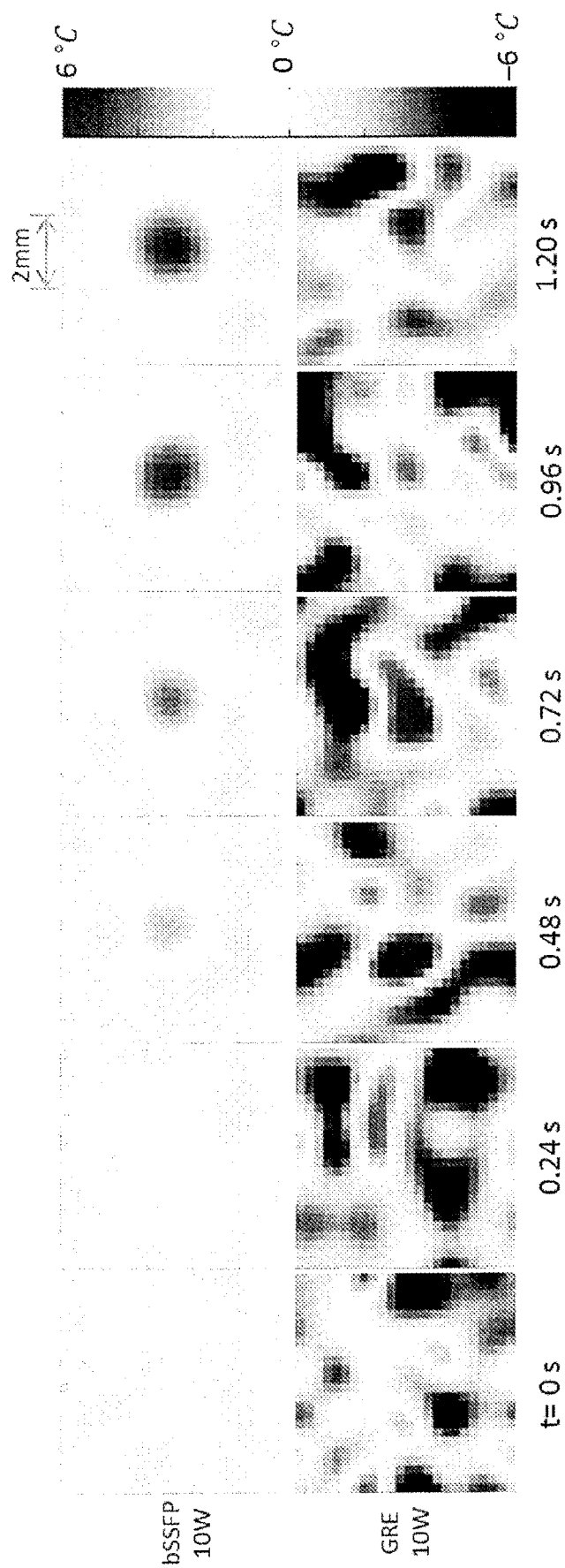
FIG. 9 shows, with respect to Example 1, 2D temperature maps during a short sonication. The spatial resolution is interpolated from 1 mm to 0.25 mm for display.

A first example (hereinafter referred to as "Example 1") of practicing aspects of the present disclosure will now be described along with corresponding results and with reference to illustrations in FIGS. 7-9.

Experiments were performed in a gel phantom using an MR-compatible 1 MHz FUS system with integrated RF coil (RK-100, FUS Instruments Inc., Toronto) and 3T MR whole-body scanner (Siemens Trio). To demonstrate that bSSFP thermometry can deliver quantitative accuracy similar to the conventional GRE method, both pulse sequences were used to monitor focal heating during a 10 s, 4 W sonication. The GRE pulse sequence parameters (TR/TE=17/9 ms with a FA=15°) provided a temporal resolution of 1 s, whereas the bSSFP pulse sequence parameters (TR/TE=4/2 ms with a FA=4°) provided a temporal resolution of 0.24 s. FIG. 7 shows the measured temperature evolution at the center of the focal spot for 10 s sonication at 4 W. The bSSFP acquisition has four times better temporal resolution than that of GRE.

To demonstrate the advantage of bSSFP over GRE for precisely measuring transient temperature rises, both pulse sequences were used to monitor focal heating due to ultrasound pulses lasting only 1 s, using a frame rate of 4 images per second. Both pulse sequences had TE=2.2 ms and TR=4.4 ms, yielding a frame rate of 4 images per second. The GRE pulse sequence had flip angle=8°, while the bSSFP pulse sequence had flip angle=4°. Sonications at 6 W, 10 W, and 14 W were applied and images were collected continuously for 10 s, starting roughly 1.25 s before each sonication. FIG. 8 shows the temperature evolution at the center of the focal spot for is sonication pulses with different powers. The GRE and bSSFP pulse sequences have the same temporal resolution. The bSSFP measurements clearly depict the transient focal heating at all powers, while the GRE measurements were dominated by noise even at the highest power. FIG. 9 shows the evolution of 2D temperature maps during a 1 s sonication at 10 W, measured with GRE and bSSFP pulse sequences with the same frame rate. The bSSFP measurements showed the temperature increase and heat dissipation, while the GRE temperature maps were dominated by noise.

Example 2

Figure 10:
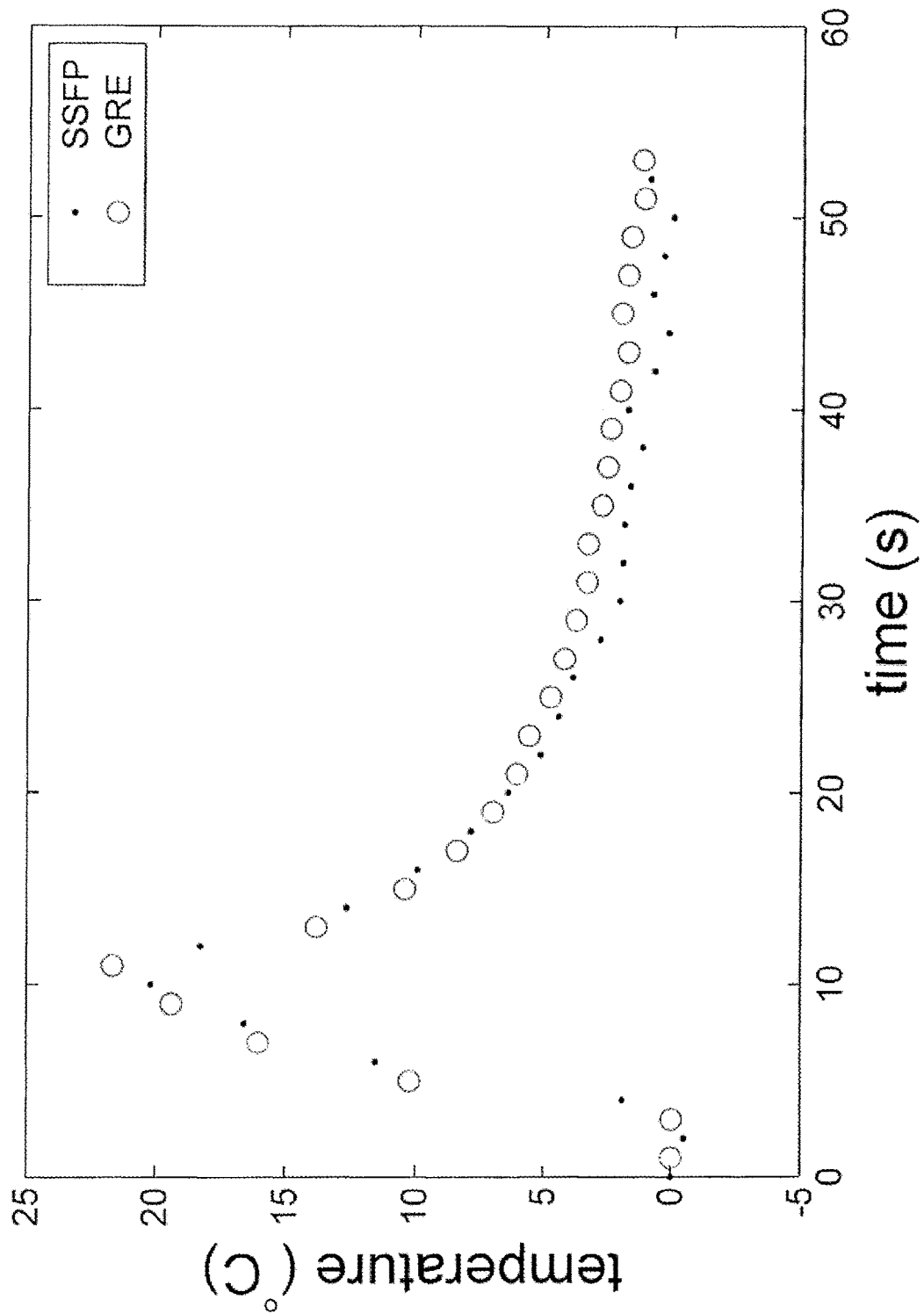
FIG. 10 illustrates temperature evolution during 10 s, 10 W sonication measured by interleaved bSSFP/GRE image acquisitions, in accordance with an example implementation of some aspects of the present disclosure that is also referred to herein as "Example 2".

A second example (hereinafter referred to as "Example 2") of practicing aspects of the present disclosure will now be described along with corresponding results and with reference to illustrations in FIGS. 10-12.

For a bSSFP pulse sequence without phase cycling, the theoretical image phase at TE=TR/2 is $$\emptyset = \tan^{-1}((E_2 \sin \beta)(1-E_2 \cos \beta)) + \beta/2 \quad [\text{Eq. 6}]$$

where $E_2 = e^{-TR/T_2}$, $\beta = 2\pi \Delta f TR$, and $\Delta f$ is the difference between the true resonance frequency and the operating frequency, often referred to as the off-resonance frequency. The bSSFP image phase undergoes an abrupt transition near resonance ($\Delta f=0$ Hz) (see FIG. 11). The on-resonance phase slope is $(d\emptyset)/(d(\Delta f))=2\pi T_2$, resulting in higher sensitivity than the GRE method, which has a TE-dependent phase slope of $2\pi TE$. Although the bSSFP phase behavior is nonlinear in the $\Delta f$ and depends on the properties of the tissue (namely $T_2$), its functional form can be measured by acquiring a series of bSSFP images with different effective frequency offsets $\Delta f$. By performing this calibration procedure as a pre-scan, the phase changes observed during the heating can be accurately converted to temperature changes over the range of frequencies spanning the bSSFP phase transition. Thus the intrinsic temperature range over which this technique may be applicable is limited by the bandwidth of the transition and varies with tissue type. However, there are methods to expand the measurable temperature range, discussed above.

Experiments were performed in a hydrogel phantom using an MR-compatible 1 MHz focused ultrasound system with integrated RF coil (RK-100, FUS Instruments Inc., Toronto) and a 3T whole-body scanner (Siemens Trio). Pulse sequence parameters for all bSSFP acquisitions included: flip angle=6°, TR/TE=4.2/2.1 ms, BW=579 Hz/px, with in-plane resolution=1 mm and slice thickness=3 mm First, the phase transition curves were measured by acquiring a series of bSSFP images, each at a different value of $\Delta f$ ranging from −50 Hz to 50 Hz in steps of 1 Hz. The phase transition curves at each pixel were fit to Eq. 3 and used for subsequent temperature calibration. To demonstrate that the bSSFP thermometry method can deliver quantitative accuracy similar to the conventional GRE method, a custom pulse sequence was constructed which alternated complete bSSFP image acquisitions with complete GRE acquisitions, and this hybrid pulse sequence was used to monitor focal heating during a 10 W, 10 s sonication. The GRE acquisitions had the same resolution and FOV as the bSSFP scans but with flip angle=20°, TR/TE=17.7/10 ms, BW=80 Hz/px. To demonstrate the advantage of bSSFP over GRE for precisely measuring transient temperature rises, both methods were used to monitor focal heating due to ultrasound pulses lasting only 1 s. Short TR and high bandwidth were used for the bSSFP sequence, yielding 4 images per second. The GRE image acquisition had TR/TE=16/7.8 ms, BW=80 Hz/pixel, and the frame rate was 1 image per second.

Figure 11:
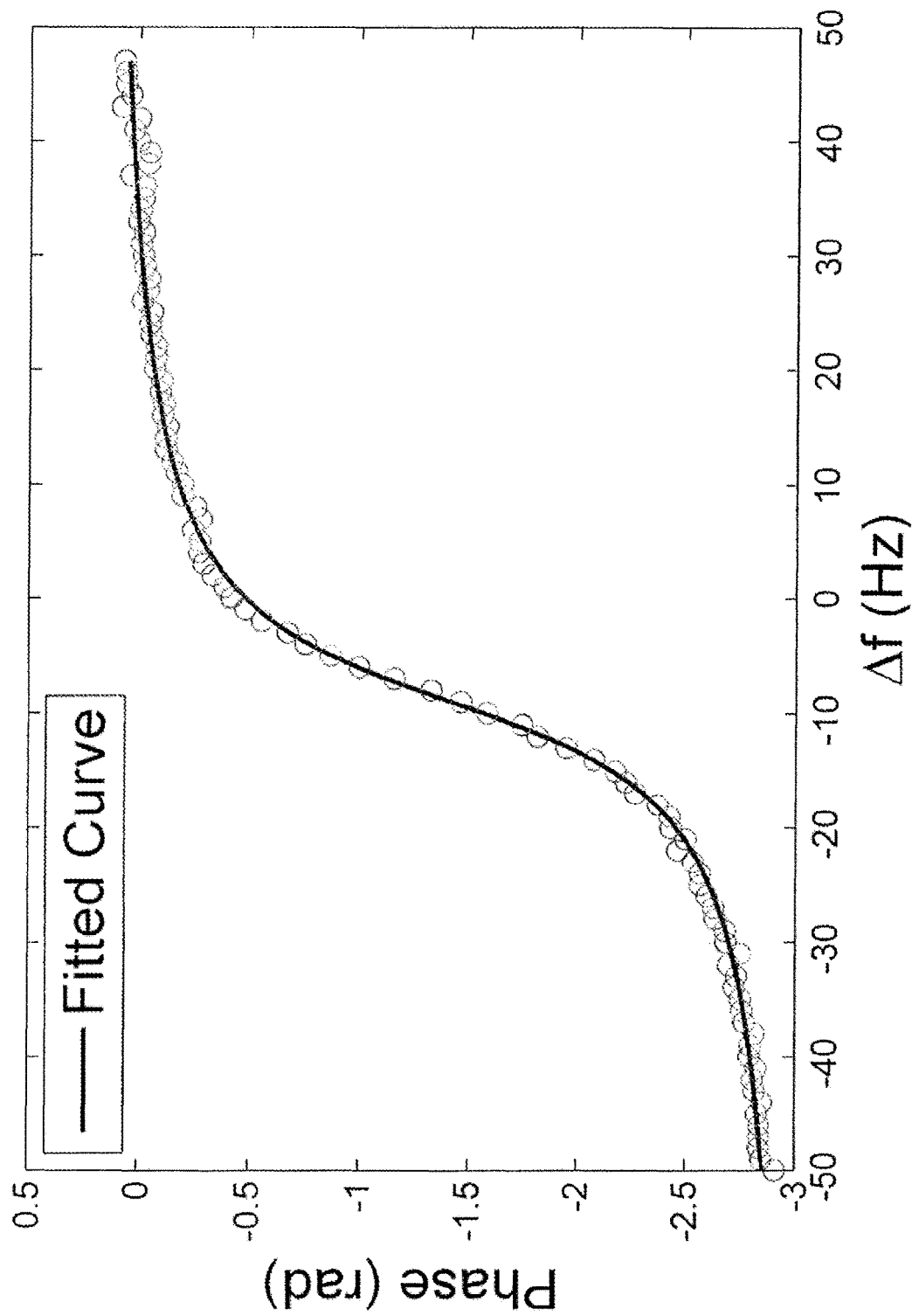
FIG. 11 illustrates, with respect to Example 2, a bSSFP phase transition curve measured in a gel phantom.
Figure 12:
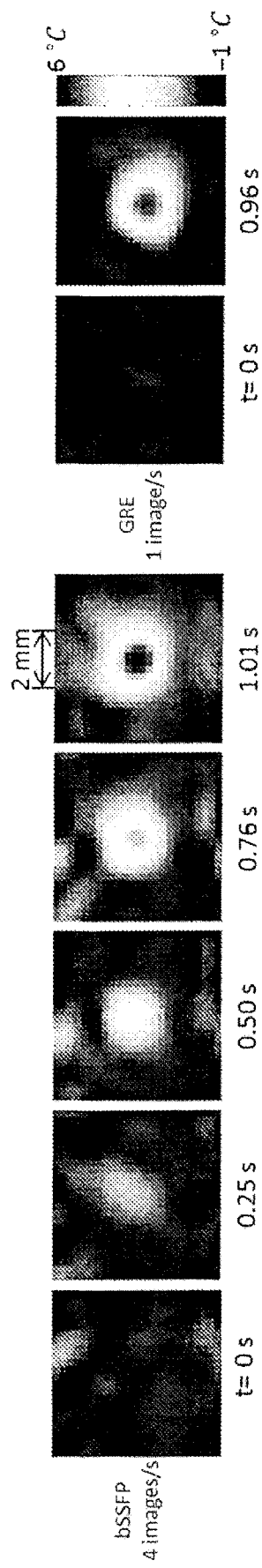
FIG. 12 shows, with respect to Example 2, 2D temperature maps during 1 s sonications at 10 W measured by fast bSSFP and slow GRE pulse sequences.

FIG. 11 shows the measured bSSFP phase transition curve at a single pixel near the focal spot, along with a fit to Eq. 3. FIG. 10 shows the temperature evolution at the focal spot for the 10 s sonication. The temperature change measured by the bSSFP method fell on the same curve as the GRE method, demonstrating the potential for a similar level of accuracy using bSSFP thermometry. FIG. 12 shows the 2D temperature maps measured by the fast bSSFP and slow GRE pulse sequences during 1 s sonication at 10 W. The bSSFP temperature maps clearly show the rapid temperature increase and sharp, transient temperature profile across the focal spot, while the GRE temperature map fails to capture this level of detail due to its low temporal resolution.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The scope of the present disclosure is indicated by the appended claims, rather than the foregoing description, and all changes that come within the meaning and range of equivalents thereof are intended to be embraced therein.

REFERENCE LIST

[1] De Poorter J, De Wagter C, De Deene Y, Thomsen C, Ståhlberg F, Achten E. Noninvasive MRI thermometry with the proton resonance frequency (PRF) method: in vivo results in human muscle. Magn Reson Med. 1995; 33:74-81.

[2] Rieke V, Vigen K K, Sommer G, Daniel B L, Pauly J M, Butts K. Referenceless PRF shift thermometry. Magn Reson Med. 2004; 51:1223-1231.

[3] Scheffler K. Fast frequency mapping with balanced SSFP: theory and application to proton-resonance frequency shift thermometry. Magn Reson Med. 2004 June; 51(6):1205-11.

[4] Rieke V, Hargreaves B A, and Pauly K B. PRF shift thermometry using multiple-acquisition phase-cycled balanced SSFP. ISMRM conference abstract 2007.

[5] Haacke E M, Brown R W, Thompson M R, Venkatesan R. Magnetic Resonance Imaging Physical Principles and Sequence Design. Wiley-Liss, 1999.

[6] Paliwal V1, El-Sharkawy A M, Du X, Yang X, Atalar E. SSFP-based MR thermometry. Magn Reson Med. 2004 October; 52(4):704-8.

[7] Bieri O, Scheffler K. Fundamentals of Balanced Steady State Free Precession MRI. J Magn Reson Imaging. 2013; 38:2-11.

[8] McDannold and Maier. Med Phys 2008; 35:3748-3758.

What is claimed is:

1. A method for magnetic resonance thermometry, comprising:
   applying a preliminary balanced steady state free precession (bSSFP) magnetic resonance imaging pulse sequence to an area of interest of a subject, the preliminary bSSFP magnetic resonance imaging pulse sequence being configured to directly measure bSSFP image phase data for a plurality of different frequencies within a predetermined range of frequencies that includes the resonance frequency associated with a target area that is within the area of interest;
   determining, based on the directly measured bSSFP image phase data, a relationship between the resonance frequency and image phase associated with the area of interest, and wherein determining the relationship comprises calculating a phase transition curve from directly measured image phase data associated with the target area for a range of resonance frequencies corresponding to a phase transition band;

applying a bSSFP magnetic resonance imaging pulse sequence to directly measure image phase data at a time point that is subsequent to the direct measurement of the image phase data for calculating the phase transition curve, in the area of interest during and/or after focused energy is applied to the subject, wherein the focused energy produces a temperature change in the target area and an associated image phase change, wherein the image phase change produced by the focused energy occurs between (i) a time of the direct measurement of the image phase data for calculating the phase transition curve and (ii) the subsequent time point;

based at least in part on the phase transition curve, determining a proton resonance frequency shift corresponding to the image phase change produced by the focused energy; and determining the temperature change in the target area based on the proton resonance frequency shift.

2. The method of claim 1, wherein the plurality of different frequencies correspond to off-resonance frequencies defined by a difference between an actual resonance frequency associated with the target area and an operating frequency used for applying the preliminary bSSFP magnetic resonance imaging pulse sequence and/or the bSSFP magnetic resonance imaging pulse sequence for temperature change measurement.

3. The method of claim 1, wherein the bSSFP magnetic resonance imaging pulse sequence for temperature change measurement uses an operating frequency determined based on the relationship between frequency and image phase associated with the area of interest determined using the preliminary bSSFP magnetic resonance imaging pulse sequence.

4. The method of claim 1, further comprising:
prior to applying the preliminary bSSFP magnetic resonance imaging pulse sequence and prior to the focused energy being applied to the subject, determining the predetermined range of frequencies by measuring resonance frequencies associated with the area of interest.

5. The method of claim 1, wherein determining the image phase change comprises acquiring, using the bSSFP magnetic resonance imaging pulse sequence for temperature change measurement, a time series of images of the area of interest before, during, and/or after the application of the focused energy and correlating phase change to resonance frequency shift for one or more pixels of the time series of images.

6. The method of claim 1, wherein the applied focused energy comprises at least one of focused ultrasound and RF electromagnetic signals.

7. The method of claim 1, further comprising:
generating, based on the determined temperature change, one or more visual representations of the temperature associated with the target area before, during, and/or after the application of the focused energy.

8. The method of claim 7, wherein generating the one or more visual representations comprises generating one or more color maps showing temperature at a plurality of different locations proximate the target area at various points in time before, during, and/or after the application of the focused energy.

9. The method of claim 1, wherein the predetermined range of frequencies is set based on an expected range of temperatures to result from application of the focused energy to the target area.

10. The method of claim 1, further comprising:
controlling an operating parameter of a source of the focused energy, while the focused energy is being applied, based on the determined temperature change.

11. The method of claim 1, further comprising:
dynamically adjusting, during the application of the focused energy, an operating frequency used for the bSSFP magnetic resonance imaging pulse sequence for temperature change measurement based on the determined temperature change.

12. The method of claim 11, wherein dynamically adjusting the operating frequency comprises manipulating phases of RF pulses applied during the bSSFP magnetic resonance imaging pulse sequence for temperature change measurement.

13. The method of claim 1, wherein the temperature change comprises heating and/or cooling of the target area.

14. The method of claim 1, wherein the target area comprises biological tissue.

15. The method of claim 1, wherein the image phase data that is directly measured at the subsequent time point is image phase data for a single image, and wherein the image phase change is determined according to image phase data consisting of the image phase data directly measured for the phase transition curve and the image phase data for the single image.

* * * * *